United States Patent [19]
Weichert et al.

[11] Patent Number: 6,011,063
[45] Date of Patent: Jan. 4, 2000

[54] ORTHO-SUBSTITUTED BENZOYLGUANIDINES, PROCESS FOR THEIR PREPARATION, THEIR USE AS A MEDICAMENT OR DIAGNOSTIC, AND MEDICAMENT COMPRISING THEM

[75] Inventors: Andreas Weichert, Egelsbach; Joachim Brendel, Bad Vilbel; Heinz-Werner Kleemann, Bischofsheim; Hans Jochen Lang, Hofheim; Jan-Robert Schwark, Frankfurt; Udo Albus, Florstadt; Wolfgang Scholz, Eschborn, all of Germany

[73] Assignee: Hoechst Aktiengesellschaft, Frankfurt am Main, Germany

[21] Appl. No.: 08/868,077

[22] Filed: Jun. 3, 1997

[30] Foreign Application Priority Data

Jun. 4, 1996 [DE] Germany ............................ 196 22 370

[51] Int. Cl.⁷ .................... A61K 31/275; A61K 31/22; A61K 31/24
[52] U.S. Cl. ................ 514/534; 514/307; 514/309; 514/311; 514/312; 514/350; 514/351; 514/522; 546/141; 546/145; 546/157; 546/170; 546/175; 546/290; 546/298; 546/300; 558/415; 560/100; 560/106; 560/251
[58] Field of Search .................... 514/307, 309, 514/311, 312, 350, 351, 522, 534; 546/141, 145, 157, 170, 175, 290, 298, 300; 558/415; 560/100, 106, 251

[56] References Cited

FOREIGN PATENT DOCUMENTS

| 0668265 | 8/1994 | Australia . |
| 9455229 | 8/1994 | Australia . |
| 0 612 723 | 8/1994 | European Pat. Off. . |
| 0 628 543 | 12/1994 | European Pat. Off. . |
| 0 690 048 | 1/1996 | European Pat. Off. . |

*Primary Examiner*—Peter O'Sullivan
*Attorney, Agent, or Firm*—Finnegan, Henderson, Farabow, Garrett & Dunner, L.L.P.

[57] ABSTRACT

Ortho-substituted benzoylguanidines of the formula I

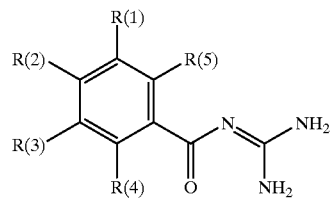

in which R(1) to R(5) have the meanings given in the claims, are suitable as antiarrhythmic pharmaceuticals having a cardioprotective component for infarct prophylaxis and for infarct treatment and also for the treatment of angina pectoris. They also inhibit in a preventive manner the pathophysiological processes in the formation of ischemically induced damage, in particular in the illicitation of ischemically induced cardiac arrhythmias.

19 Claims, No Drawings

ORTHO-SUBSTITUTED BENZOYLGUANIDINES, PROCESS FOR THEIR PREPARATION, THEIR USE AS A MEDICAMENT OR DIAGNOSTIC, AND MEDICAMENT COMPRISING THEM

SUMMARY OF THE INVENTION

The invention relates to benzoylguanidines of the formula I $$\text{I}$$

[Structure showing benzene ring with substituents R(1), R(2), R(3), R(4), R(5) and a C(=O)-N=C(NH$_2$)-NH$_2$ group]

in which:
R(1) is H, F, Cl, Br, I, CN, NO$_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or $X_a$—(CH$_2$)$_b$—(CF$_2$)$_c$—CF$_3$;
X is oxygen, sulfur or NR(9);
a is zero or 1;
b is zero, 1 or 2;
c is zero, 1, 2 or 3;
R(9) is H, alkyl having 1, 2, 3 or 4 carbon atoms or —C$_d$H$_{2d}$R(6);
d is zero, 1, 2, 3 or 4;
R(6) is cycloalkyl having 3, 4, 5, 6, 7 or 8 carbon atoms, phenyl, biphenylyl or naphthyl,
where the aromatic radicals phenyl, biphenylyl or naphthyl are not substituted or are substituted by 1–3 substituents selected from the group consisting of F, Cl, CF$_3$, methyl, methoxy and NR(7)R(8);
R(7) and R(8)
being, independently, H or alkyl having 1, 2, 3 or 4 carbon atoms;

or
R(1) is —SR(10), —OR(10) or —CR(10)R(11)R(12);
R(10) is —C$_f$H$_{2f}$-cycloalkyl having 3, 4, 5, 6, 7 or 8 carbon atoms in the cycloalkyl ring, heteroaryl having 1, 2, 3, 4, 5, 6, 7, 8 or 9 carbon atoms or phenyl, where heteroaryl and phenyl are unsubstituted or are substituted by 1–3 substituents selected from the group consisting of F, Cl, CF$_3$, CH$_3$, methoxy, hydroxyl, amino, methylamino and dimethylamino;
f is zero, 1 or 2;
R(11) and (R12)
independently of each other, are defined as R(10) or are hydrogen or alkyl having 1, 2, 3 or 4 carbon atoms;

or
R(1) is phenyl, naphthyl, biphenylyl or heteroaryl having 1, 2, 3, 4, 5, 6, 7, 8, or 9 carbon atoms, the latter linked via a carbon or nitrogen atom of the ring,
each of which is unsubstituted or is substituted by 1–3 substituents selected from the group consisting of F, Cl, CF$_3$, CH$_3$, methoxy, hydroxyl, amino, methylamino and dimethylamino;

or
(R1) is —SR(13), —OR(13), —NHR(13), —NR(13)R(14), —CHR(13)R(15), —[CR(15)R(16)]OH, —C≡CR(18), —C[R(19)]=CHR(18), —C[R(20)R(21)]$_k$—(CO)—[CR(22)R(23)]$_l$—R(24),
k is zero, 1, 2, 3 or 4;
l is zero, 1, 2, 3 or 4;
R(13) and R(14)
identically or differently, are —(CH$_2$)$_g$—(CHOH)$_h$—(CH$_2$)$_i$—(CHOH)$_{kk}$—R(17) or —(CH$_2$)$_g$—O—(CH$_2$—CH$_2$O)$_{h-R}$(24);
R(17) is hydrogen or methyl;
g, h and l,
identically or differently, are zero, 1, 2, 3 or 4;
kk is 1, 2, 3 or 4;
R(15) and R(16),
identically or differently, are hydrogen, alkyl having 1, 2, 3, 4, 5 or 6 carbon atoms, or, together with the carbon atom carrying them, cycloalkyl having 3, 4, 5, 6, 7 or 8 carbon atoms;
R(18) is phenyl,
which is unsubstituted or is substituted by 1–3 substituents selected from the group consisting of F, Cl, CF$_3$, methyl, methoxy and NR(25)R(26);
R(25) and R(26)
are H or alkyl having 1, 2, 3 or 4 carbon atoms;

or
R(18) is heteroaryl having 1, 2, 3, 4, 5, 6, 7, 8 or 9 carbon atoms,
which is unsubstituted or is substituted as phenyl;

or
R(18) is alkyl having 1, 2, 3, 4, 5 or 6 carbon atoms, which is unsubstituted or is substituted by 1–3 OH;

or
R(18) is cycloalkyl having 3, 4, 5, 6, 7 or 8 carbon atoms;
R(19), R(20), R(21), R(22) and R(23),
identically or differently, are hydrogen or methyl;
R(24) is H, alkyl having 1, 2, 3, 4, 5 or 6 carbon atoms, cycloalkyl having 3, 4, 5, 6, 7 or 8 carbon atoms or —C$_m$H$_{2m}$—R(18);
m is 1, 2, 3 or 4;
one of the two substituents R(2) and R(3)
is —O—CO—R(27);
R(27) is alkyl having 1, 2, 3, 4, 5, 6, 7 or 8 carbon atoms, cycloalkyl having 3, 4, 5, 6, 7 or 8 carbon atoms, phenyl, biphenylyl, naphthyl, pyridyl or quinolinyl,
where phenyl, biphenylyl, naphthyl, pyridyl or quinolyl are unsubstituted or substituted by 1–3 substituents selected from the group consisting of F, Cl, CF$_3$, methyl, methoxy and NR(7)R(8);
R(7) and R(8)
independently of one another are hydrogen or alkyl having 1, 2, 3 or 4 carbon atoms;
where one of the substituents R(2) and R(3) is always defined as R(1);
R(4) and R(5)
independently of one another are hydrogen, alkyl having 1, 2, 3 or 4 carbon atoms, alkoxy having 1, 2, 3 or 4 carbon atoms, F, Cl, Br, I, CN or —(CH$_2$)$_n$—(CF$_2$)$_o$—CF$_3$;
n is zero or 1;
o is zero or 1;
and their pharmaceutically tolerable salts.

Preferred compounds of the formula I are those in which:

R(1) is H, F, Cl, Br, I, CN, $NO_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or $X_a$—$(CF_2)_c$—$CF_3$;
X is oxygen or sulfur;
a is zero or 1;
c is zero, 1, 2 or 3;

or

R(1) is —SR(10) or —OR(10);
R(10) is —$C_fH_{2f}$-cycloalkyl having 3, 4, 5, 6, 7 or 8 carbon atoms in the cycloalkyl ring, heteroaryl having 1, 2, 3, 4, 5, 6, 7, 8 or 9 carbon atoms or phenyl, where heteroaryl and phenyl are unsubstituted or are substituted by 1–3 substituents selected from the group consisting of F, Cl, $CF_3$, $CH_3$, methoxy, hydroxyl, amino, methylamino and dimethyl-amino;
f is zero or 1;

or

R(1) is phenyl, naphthyl, biphenylyl or heteroaryl having 1, 2, 3, 4, 5, 6, 7, 8 or 9 carbon atoms, the latter linked via a carbon or nitrogen atom of the ring, each of which is unsubstituted or is substituted by 1–3 substituents selected from the group consisting of F, Cl, $CF_3$, $CH_3$, methoxy, hydroxyl, amino, methylamino and dimethylamino;

or (R1) is —SR(13), —OR(13), —NHR(13), —NR(13)R(14), —C≡CR(18) or —C[R(19)]=CHR(18);
R(13) and R(14),
identically or differently, are —$(CH_2)_g$—$(CHOH)_h$—$(CH_2)_i$—$(CHOH)_{kk}$—R(17) or —$(CH_2)_g$—O—$(CH_2$—$CH_2O)_h$—R(24);
R(17) is hydrogen or methyl;
g, h and i,
identically or differently, are zero, 1 or 2;
kk is 1 or 2;
R(18) is phenyl,
which is unsubstituted or is substituted by 1–3 substituents selected from the group consisting of F, Cl, $CF_3$, methyl, methoxy and NR(25)R(26);
R(25) and R(26)
are H or alkyl having 1, 2, 3 or 4 carbon atoms;

or

R(18) is heteroaryl having 1, 2, 3, 4, 5, 6, 7, 8 or 9 carbon atoms,
which is unsubstituted or is substituted as phenyl;

or

R(18) is cycloalkyl having 3, 4, 5, 6, 7 or 8 carbon atoms;
R(19) is hydrogen or methyl;
one of the substituents R(2) and R(3)
is —O—CO—R(27);
R(27) is alkyl having 1, 2, 3 or 4 carbon atoms, cycloalkyl having 3, 4, 5 or 6 carbon atoms, phenyl, biphenylyl, naphthyl, pyridyl or quinolinyl,
where phenyl, biphenylyl, naphthyl, pyridyl or quinolinyl are unsubstituted or substituted by 1–3 substituents selected from the group consisting of F, Cl, $CF_3$, methyl and methoxy;

and the other of the substituents R(2) and R(3) in each case is defined as R(1);
R(4) and R(5)
are hydrogen, alkyl having 1 or 2 carbon atoms, alkoxy having 1 or 2 carbon atoms, F, Cl, CN or —$(CF_2)_o$—$CF_3$;

o is zero or 1;

where R(4) and R(5) are not simultaneously hydrogen and their pharmaceutically tolerable salts.

Particularly preferred compounds of the formula I are those in which:

R(1) is H, F, Cl, alkyl having 1, 2, 3 or 4 carbon atoms, alkoxy having 1, 2, 3 or 4 carbon atoms, cycloalkyl having 5 or 6 carbon atoms or $X_a$—$CF_3$;
X is oxygen;
a is zero or 1;

or

R(1) is —SR(10) or —OR(10);
R(10) is cycloalkyl having 4, 5 or 6 carbon atoms, quinolyl, isoquinolyl, pyridyl or phenyl,
quinolyl, isoquinolyl and pyridyl being bonded via a carbon or nitrogen atom of their ring,
and phenyl being unsubstituted or substituted by 1–3 substituents selected from the group consisting of F, Cl, $CF_3$, $CH_3$, methoxy, hydroxyl, amino, methylamino and dimethylamino;

or

R(1) is quinolyl, isoquinolyl or pyridyl,
each of which is linked via a carbon or nitrogen atom of their ring, or (R1) is —C≡CR(18);
R(18) is phenyl or cycloalkyl having five or 6 carbon atoms,
R(2) and R(3) are
—O—CO—R(27);
R(27) is alkyl having 1, 2, 3 or 4 carbon atoms, cycloalkyl having 3, 4, 5 or 6 carbon atoms, phenyl, biphenylyl, naphthyl, pyridyl or quinolinyl,
where phenyl, biphenylyl, naphthyl, pyridyl or quinolinyl are unsubstituted or substituted by 1–3 substituents selected from the group consisting of F, Cl, $CF_3$, methyl and methoxy;
where one of the substituents R(2) and R(3) is always defined as R(1);
R(4) and R(5)
independently of one another are methyl, methoxy, F, Cl, CN or $CF_3$; and their pharmaceutically tolerable salts.

Very particularly preferred compounds of the formula I are those in which

R(1) is H, F, Cl, alkyl having 1, 2, 3 or 4 carbon atoms, alkoxy having 1, 2, 3 or 4 carbon atoms, cycloalkyl having 5 or 6 carbon atoms, cycloalkoxy having 5 or 6 carbon atoms or $CF_3$;
one of the substituents R(2) and R(3) is

—O—CO—$CH_3$;

and the other of the substituents R(2) and R(3) in each case is defined as R(1);
R(4) and R(5) are
methyl, methoxy, F, Cl, CN or $CF_3$;
where R(4) and R(5)
are not simultaneously hydrogen;
and their pharmaceutically tolerable salts.

DETAILED DESCRIPTION OF THE INVENTION

Heteroaryl having 1, 2, 3, 4, 5, 6, 7, 8 or 9 carbon atoms is understood to mean radicals which are derived from phenyl or naphthyl, in which one or more CH groups are replaced by N and/or in which at least two neighboring CH groups (with the formation of a five-membered aromatic ring) are replaced by S, NH or O. In addition, one or both the atoms of the fusion site of bicyclic radicals (as in indolizinyl) can also be N atoms. It applies, in particular, that heteroaryl having 1, 2, 3, 4, 5, 6, 7, 8 or 9 carbon atoms is furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl or cinnolinyl; particularly furanyl, thienyl, pyrrolyl, imidazolyl, pyrazolyl, triazolyl, thiazolyl, pyridyl, indolyl, quinolyl and isoquinolyl.

If one of the substituents R(1) to R(5) contains one or more centers of asymmetry, these centers can have either the S-configuration or the R-configuration. The compounds can be present as optical isomers, as diastereomers, as racemates or as mixtures thereof.

The designated alkyl radicals can be straight-chain or branched.

In addition, a process of preparing intermediates of compound (I) wherein R(2) or R(3) are OH is provided which comprises reacting a compound of the formula II

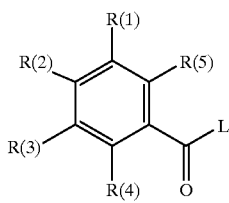

wherein R(2) or R(3) are OH and R(1) to R(5) have the otherwise given and L is a leaving group which can readily be substituted nucleophilically, with guanidine.

The activated acid derivatives of the formula 11, in which L is an alkoxy, preferably a methoxy, group, a phenoxy group, phenylthio, methylthio or 2-pyridylthio group, or a nitrogen heterocycle, preferably 1-imidazolyl, are advantageously obtained, in a manner known per se, from the underlying carbonyl chlorides (formula II, L=Cl), which, for their part, can in turn be prepared, in a manner known per se, from the underlying carboxylic acids (formula II, L=OH), for example using thionyl chloride.

In addition to the carbonyl chlorides of the formula II (L=Cl), further activated acid derivatives of the formula II can also be prepared, in a manner known per se, directly from the underlying benzoic acid derivatives (formula II, L=OH), such as the methyl esters of the formula II with L=OCH$_3$ by treating with gaseous HCl in methanol, the imidazolides of the formula II by treating with carbonyldiimidazole [L=1-imidazolyl, Staab, Angew. Chem. Int. Ed. Engl. 1, 351–367 (1962)], the mixed anhydrides II with Cl—COOC$_2$H$_5$ or tosyl chloride in the presence of triethylamine in an inert solvent, as well as the activation of benzoic acids with dicyclohexylcarbodiimide (DCC) or with O—[(cyano(ethoxycarbonyl)methylene)amino]-1,1,3,3-tetramethyluronium tetrafluoroborate ("TOTU") [Proceedings of the 21. European Peptide Symposium, Peptides 1990, Editors E. Giralt and D. Andreu, Escom, Leiden, 1991]. A number of suitable methods for preparing activated carboxylic acid derivatives of the formula II are given, with details of source literature, in J. March, Advanced Organic Chemistry, Third Edition (John Wiley & Sons, 1985), p. 350.

The reaction of an activated carboxylic acid derivative of the formula II with guanidine is effected, in a manner known per se, in a protic or aprotic organic solvent which is polar but inert. In this context, methanol, isopropanol or THF have proved to be suitable, at temperatures of from 20° C. up to the boiling temperature of these solvents, for use in the reaction of the methyl benzoates (II, L=OMe) with guanidine. Most reactions of compounds II with salt-free guanidine are advantageously carried out in aprotic, inert solvents, such as THF, dimethoxyethane and dioxane. However, water can also be used, employing a base, such as, for example, NaOH, as solvent in the reaction of II with guanidine.

When L=Cl, an acid scavenger, for example in the form of excess guanidine, is advantageously added in order to bind the hydrohalic acid.

Some of the underlying benzoic acid derivatives of the formula II are known and are described in the literature. The unknown compounds of the formula II may be prepared by methods known from the literature. The resulting benzoic acids are reacted to give compounds I according to the invention in accordance with one of the above-described process variants.

The introduction of some substituents in the 2, 3, 4 and 5 positions is achieved by methods known from the literature involving palladium-mediated cross-coupling of aryl halides or aryl triflates with, for example, organostannanes, organoboronic acids or organoboranes or organocopper or organozinc compounds.

In general, benzoylguanidines I are weak bases and can bind acid with formation of salts. Possible acid addition salts are salts of all pharmacologically tolerable acids, for example halides, in particular hydrochlorides, lactates, sulfates, citrates, tartrates, acetates, phosphates, methanesulfonates and p-toluenesulfonates.

The compounds I are substituted acylguanidines.

Compounds similar to the compounds I are disclosed in European Offenlegungsschrift 612 723 A1 (HOE 93/F 054). These already contain hydroxyl groups as substituents in the phenyl nucleus, but no substituents in the ortho-position.

Compared with the known compounds, the compounds according to the invention are distinguished by an extremely high activity in the inhibition of Na$^+$/H$^+$ exchange and also by improved water solubility.

Like the known compounds, they have no undesirable and disadvantageous salidiuretic properties, but very good antiarrhythmic properties, such as are important, for example, for the treatment of illnesses which occur in the case of oxygen deficiency symptoms. On account of their pharmacological properties, the compounds are outstandingly suitable as antiarrhythmic pharmaceuticals having a cardioprotective component for infarct prophylaxis and infarct treatment, and for the treatment of angina pectoris, where they also inhibit or greatly decrease in a preventive manner the pathophysiological processes in the formation of ischemically induced damage, in particular in the causation of ischemically induced cardiac arrhythmias. Because of their protective effects against pathological hypoxic and ischemic situations, the compounds of the formula I according to the invention can be used, as a result of inhibition of the cellular Na$^+$/H$^+$ exchange mechanism, as pharmaceuticals for the treatment of all acute or chronic damage caused by ischemia or illnesses induced primarily or secondarily by this means. This relates to their use as pharmaceuticals for surgical interventions, e.g. in organ transplantation, where the compounds can be used both for the protection of the organs in the donor before and during removal, for the protection of removed organs, for example during treatment with or storage thereof in physiological bath fluids, and also during transfer to the recipient's body. The compounds are also useful, protective pharmaceuticals when carrying out angioplastic surgical interventions, for example on the heart and on peripheral vessels. Corresponding to their protective action against ischemically induced damage, the compounds are also suitable as pharmaceuticals for the treatment of ischemias of the nervous system, in particular of the CNS, where they are suitable, for example, for the treatment of stroke or of cerebral edema. Moreover, the compounds of the formula I according to the invention are also suitable for the treatment of forms of shock, such as, for example, of allergic, cardiogenic, hypovolemic and of bacterial shock.

Moreover, the compounds of the formula I according to the invention are distinguished by potent inhibitory action on the proliferation of cells, for example fibroblast cell proliferation and the proliferation of vascular smooth muscle cells. The compounds of the formula I are therefore suitable as useful therapeutics for illnesses in which cell proliferation is a primary or secondary cause, and can therefore be used as antiatherosclerotics, agents against diabetic late complications, carcinomatous disorders, fibrotic disorders such as pulmonary fibrosis, hepatic fibrosis or renal fibrosis, organ hypertrophies and hyperplasias, in particular in prostate hyperplasia or prostate hypertrophy.

The compounds according to the invention are effective inhibitors of the cellular sodium-proton antiporter ($Na^+/H^+$ exchanger), which is raised in numerous disorders (essential hypertension, atherosclerosis, diabetes, etc.) even in those cells which are easily accessible to measurements, such as, for example, in erythrocytes, platelets or leucocytes. The compounds according to the invention are therefore suitable as outstanding and simple scientific tools, for example in their use as diagnostics for the determination and differentiation of certain forms of hypertension, but also of atherosclerosis, of diabetes and of proliferative disorders, etc. Moreover, the compounds of the formula I are suitable for preventive therapy for the prevention of the genesis of high blood pressure, for example of essential hypertension.

It has additionally been found that compounds of the formula I have a favorable effect on serum lipoproteins. It is generally recognized that for the formation of arteriosclerotic vascular changes, in particular of coronary heart disease, excessively high blood lipid values, so-called hyperlipoproteinemias, are a significant risk factor. For the prophylaxis and the regression of atherosclerotic changes, the lowering of raised serum lipoproteins is therefore of extreme importance. Beside the reduction of the total serum cholesterol, the lowering of the proportion of specific atherogenic lipid fractions of this total cholesterol, in particular of the low density lipoproteins (LDL) and of the very low density lipoproteins (VLDL) is of particular importance, as these lipid fractions are an atherogenic risk factor. In contrast, the high density lipoproteins are ascribed a protective function against coronary heart disease. Accordingly, hypolipidemics should be able to lower not only the total cholesterol, but in particular the VLDL and LDL serum cholesterol fractions. It has now been found that compounds of the formula I have valuable therapeutically utilizable properties with respect to the effect on the serum lipid levels. Thus they significantly lower the raised serum concentrations of LDL and VLDL, as are to be observed, for example, as a result of increased dietetic uptake of a cholesterol- and lipid-rich diet or in the case of pathological metabolic changes, for example genetically related hyperlipidemias. They can therefore be used for the prophylaxis and for the regression of atherosclerotic changes in that they eliminate a causal risk factor. These include not only the primary hyperlipidemias, but also certain secondary hyperlipidemias, such as occur, for example, in diabetes. Moreover, the compounds of the formula I lead to a marked reduction in the infarcts induced by metabolic anomalies and in particular to a significant decrease in the induced infarct size and its degree of severity. Furthermore, compounds of the formula I result in effective protection against damage due to metabolic anomalies of induced endothelial damage. With this protection of the vessels against the syndrome of endothelial dysfunction, compounds of the formula I are valuable medicaments for the prevention and for the treatment of coronary vascular spasms, of atherogenesis and of atherosclerosis, of left-ventricular hypertrophy and of dilated cardiomyopathy, and of thrombotic disorders.

The compounds mentioned are therefore advantageously used for the production of a medicament for the treatment of hypercholesterolemia, for the production of a medicament for the prevention of atherogenesis, for the production of a medicament for the prevention and treatment of atherosclerosis, for the production of a medicament for the prevention and treatment of illnesses which are caused by raised cholesterol levels, for the production of a medicament for the prevention and treatment of illnesses which are caused by endothelial dysfunction, for the production of a medicament for the prevention and treatment of atherosclerosis-induced hypertension, for the production of a medicament for the prevention and treatment of atherosclerosis-induced thromboses, for the production of a medicament for the prevention and treatment of hypercholesterolemia and endothelial dysfunction-induced ischemic damage and postischemic reperfusion damage, for the production of a medicament for the prevention and treatment of hypercholesterolemia and endothelial dysfunction-induced cardiac hypertrophies and cardiomyopathies, for the production of a medicament for the prevention and treatment of hypercholesterolemia and endothelial dysfunction-induced coronary vascular spasms and myocardial infarcts, for the production of a medicament for the treatment of the conditions mentioned in combinations with hypotensive substances, preferably with angiotensin converting enzyme (ACE) inhibitors and angiotensin receptor antagonists, a combination of an NHE inhibitor of the formula I with a blood lipid level-lowering active compound, preferably with an HMG-CoA-reductase inhibitor (e.g. lovastatin or pravastatin), the latter contributing a hypolipidemic action and thereby increasing the hypolipidemic properties of the NHE inhibitor of the formula I, proving to be a favorable combination with increased action and decreased use of active compound.

The administration of sodium-proton exchange inhibitors of the formula I as novel pharmaceuticals for lowering raised blood lipid levels is claimed, as well as the combination of sodium-proton exchange inhibitors with hypotensive and/or hypolipidemic pharmaceuticals.

Pharmaceuticals which contain a compound I can be administered orally, parenterally, intravenously or rectally, or by inhalation, the preferred route of administration being dependent on how the disorder manifests itself. In this context, the compounds I may be used alone or together with pharmaceutical auxiliary substances, both in the case of veterinary medicine and in the case of human medicine.

The person skilled in the art is familiar with which auxiliary substances are suitable for the desired pharmaceutical formulation. In addition to solvents, gel-formers, suppository bases, tablet auxiliary substances, and other active-compound excipients, antioxidants, dispersing agents, emulsifiers, defoamers, taste corrigents, preservatives, solubilizers or dyes, for example, can be used.

In order to prepare a form for oral use, the active compounds are mixed with the additives which are suitable for the purpose, such as excipient substances, stabilizers or inert diluents, and converted by the customary methods into the forms suitable for administration, such as tablets, coated tablets, hard gelatin capsules or aqueous, alcoholic or oily solutions. Gum arabic, magnesia, magnesium carbonate, potassium phosphate, lactose, glucose or starch, in particular corn starch, for example, can be used as inert carriers. In this context, the preparation can be effected as dry or wet granules. Vegetable or animal oils, for example, such as sunflower oil or cod-liver oil, are suitable for use as oily carrier substances or as solvents.

For subcutaneous or intravenous administration, the active compounds, if desired together with the substances which are customary for the purpose, such as solubilizers, emulsifiers or additional auxiliary substances, are brought into solution, suspension or emulsion. Examples of suitable solvents are: water, physiological saline solution, or alcohols, for example ethanol, propanol or glycerol, and in addition sugar solutions as well, such as glucose or mannitol solutions, or else a mixture of the various solvents mentioned.

Solutions, suspensions or emulsions of the active compound of the formula I in a pharmaceutically harmless solvent, such as, in particular, ethanol or water, or a mixture of such solvents, are suitable for use as a pharmaceutical formulation for administration in the form of aerosols or sprays, for example.

Depending on requirements, the formulation can also contain other further pharmaceutical auxiliary substances, such as surfactants, emulsifiers and stabilizers, as well as a propellant. Such a preparation customarily contains the active compound in a concentration of about 0.1 to 10, in particular of about 0.3 to 3% by weight.

The dosage of the active compound of the formula I to be administered, and the frequency of the administration, depend on the strength and the duration of the effect of the compounds used; additionally also on the nature and severity of the disease to be treated, as well as on the sex, age, weight and individual responsiveness of the mammal to be treated.

The term "Patient" means a mammal such as a dog, cat, guinea pig, mouse, rat or human being.

The terms "Treating" or "to treat" means to alleviate symptoms, eliminate the causation either on a temporary or permanent basis, or to prevent or slow the appearance of symptoms (prophylaxis).

On average, the daily dose of a compound of the formula I for a patient of about 75 kg in weight is at least 0.001 mg/kg, preferably 0.01 mg/kg, up to at most 10 mg/kg, preferably 1 mg/kg, of body weight. In acute episodes of the disorder, for example immediately after suffering a cardiac infarct, even higher, and in particular more frequent, dosages may also be necessary, for example up to 4 individual doses per day. In association with i.v. use, in particular, for example in the case of an infarct patient in intensive care, up to 200 mg per day may be necessary.

List of Abbreviations:
MeOH methanol
DMF N,N-dimethylformamide
RT room temperature
EA ethyl acetate (EtOAc)
m.p. melting point
THF tetrahydrofuran
eq. equivalent Experimental Section

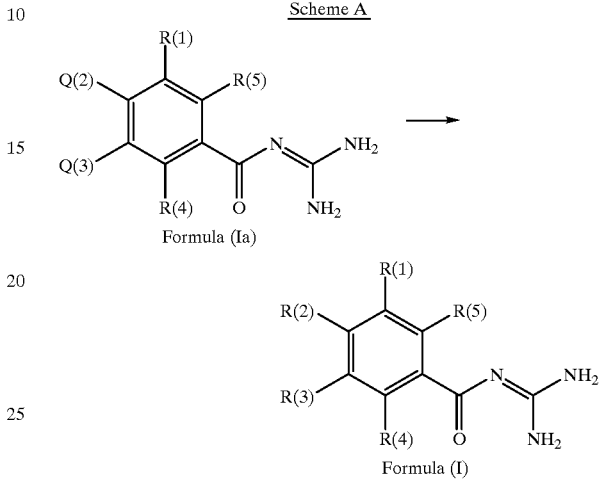

Q(2)=—OH or R(1) and
Q(3)=—OH or R(1) with the proviso that Q(2) and Q(3) cannot be —OH at the same time, and Q(2) and Q(3) cannot both be —R(1) at the same time.

General Instructions for Preparing Benzoylguanidines of Formula (I):

Scheme A; 1.0 equivalent of the hydroxylated benzoyl guanidine derivative of formula (Ia) is dissolved or suspended in a suitable anhydrous organic solvent, such as acetonitrile (8 mL/mmol), and 0.25 eq. of solid anhydrous Cobalt (II) chloride is added under an atmosphere of argon. Then 1.0 eq. of a suitable anhydride is added dropwise at a temperature between 0° C. and room temperature. Examples of suitable anhydrides are acetic anhydride, isobutyric anhydride, propionic anhydride, n-butyric anhydride, (S)-(+)-2-methylbutyric anhydride, pivalic anhydride, valeric anhydride, isovaleric anhydride, benzoic anhydride, 4-methoxybenzoic anhydride, 3,4-dimethoxybenzoic anhydride, 3,4,5-trimethoxybenzoic anhydride, bis(2,6-dichlorobenzoic) anhydride, o-toluic anhydride, m-toluic anhydride, p-chlorobenzoic anhydride and the like. The mixture is stirred for about 1 to 3 hours, until conversion is complete (Monitoring the reaction by thin layer chromatography). The product is then isolated and purified by techniques well known to one of ordinary skill in the art, such as extraction and recrystallization. For example, water is added to the reaction and the mixture is extracted with a suitable organic solvent, such as ethyl acetate (3 times). The organic extracts are then combined, dried over anhydrous sodium sulfate, filtered and partially concentrated by evaporation. A suitable organic solvent, such as diethyl ether is then added to crystallize the product of formula (I), which is collected by filtration.

What is claimed is:

1. An ortho-substituted benzoylguanidine of the formula I

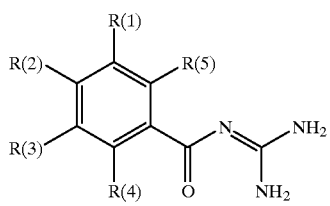

in which:
R(1) is H, F, Cl, Br, I, CN, NO$_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or X$_a$—(CH$_2$)$_b$—(CF$_2$)$_c$—CF$_3$;
X is oxygen, sulfur or NR(9);
a is zero or 1;
b is zero, 1 or 2;
c is zero, 1, 2 or 3;
  R(9) is H, alkyl having 1, 2, 3 or 4 carbon atoms or —C$_d$H$_{2d}$R(6);
  d is zero, 1, 2, 3 or 4;
    R(6) is cycloalkyl having 3, 4, 5, 6, 7 or 8 carbon atoms, phenyl, biphenylyl or naphthyl,
      where the aromatic radicals phenyl, biphenylyl or naphthyl are not substituted or are substituted by 1–3 substituents selected from the group consisting of F, Cl, CF$_3$, methyl, methoxy and NR(7)R(8);
      R(7) and R(8)
        being, independently, H or alkyl having 1, 2, 3 or 4 carbon atoms;
or
  R(1) is —SR(10), —OR(10) or —CR(10)R(11)R(12);
    R(10) is —C$_f$H$_{2f}$-cycloalkyl having 3, 4, 5, 6, 7 or 8 carbon atoms in the cycloalkyl ring, heteroaryl having 1, 2, 3, 4, 5, 6, 7, 8 or 9 carbon atoms or phenyl, where heteroaryl and phenyl are unsubstituted or are substituted by 1–3 substituents selected from the group consisting of F, Cl, CF$_3$, CH$_3$, methoxy, hydroxyl, amino, methylamino and dimethylamino;
    f is zero, 1 or 2;
    R(11) and (R12),
      independently of each other, are defined as R(10) or are hydrogen or alkyl having 1, 2, 3 or 4 carbon atoms;
or
  R(1) is phenyl, naphthyl, biphenylyl or heteroaryl having 1, 2, 3, 4, 5, 6, 7, 8, or 9 carbon atoms, the latter linked via a carbon or nitrogen atom of the ring,
    each of which is unsubstituted or is substituted by 1–3 substituents selected from the group consisting of F, Cl, CF$_3$, CH$_3$, methoxy, hydroxyl, amino, methylamino and dimethylamino;
or
  (R1) is —SR(13), —OR(13), —NHR(13), —NR(13)R(14), —CHR(13)R(15), —C[R(15)R(16)]OH, —C≡CR(18), —C[R(19)]=CHR(18), —[CR(20)R(21)]$_k$—(CO)—[CR(22)R(23)]$_l$—R(24),
  k is zero, 1, 2, 3 or 4;
  l is zero, 1, 2, 3 or 4;

R(13) and R(14),
  identically or differently, are —(CH$_2$)$_g$—(CHOH)$_h$—(CH$_2$)$_i$—(CHOH)$_{kk}$—R(17) or —(CH$_2$)$_g$—O—(CH$_2$—CH$_2$O)$_h$—R(24);
R(17) is hydrogen or methyl;
g, h and l,
  identically or differently, are zero, 1, 2, 3 or 4;
kk is 1, 2, 3 or 4;
R(15) and R(16),
  identically or differently, are hydrogen, alkyl having 1, 2, 3, 4, 5 or 6 carbon atoms, or, together with the carbon atom carrying them, cycloalkyl having 3, 4, 5, 6, 7 or 8 carbon atoms;
R(18) is phenyl,
  which is unsubstituted or is substituted by 1–3 substituents selected from the group consisting of F, Cl, CF$_3$, methyl, methoxy and NR(25)R(26);
    R(25) and R(26)
      are H or alkyl having 1, 2, 3 or 4 carbon atoms;
or
R(18) is heteroaryl having 1, 2, 3, 4, 5, 6, 7, 8 or 9 carbon atoms,
  which is unsubstituted or is substituted as phenyl;
or
R(18) is alkyl having 1, 2, 3, 4, 5 or 6 carbon atoms, which is unsubstituted or is substituted by 1–3 OH;
or
R(18) is cycloalkyl having 3, 4, 5, 6, 7 or 8 carbon atoms;
R(19), R(20), R(21), R(22) and R(23),
  identically or differently, are hydrogen or methyl;
R(24) is H, alkyl having 1, 2, 3, 4, 5 or 6 carbon atoms, cycloalkyl having 3, 4, 5, 6, 7 or 8 carbon atoms or —C$_m$H$_{2m}$—R(18);
  m is 1, 2, 3 or 4;
one of the two substituents R(2) and R(3) is
  —O—CO—R(27);
R(27) is alkyl having 1, 2, 3, 4, 5, 6, 7 or 8 carbon atoms, cycloalkyl having 3, 4, 5, 6, 7 or 8 carbon atoms, phenyl, biphenylyl, naphthyl, pyridyl or quinolinyl,
  where phenyl, biphenylyl, naphthyl, pyridyl or quinolyl are unsubstituted or substituted by 1–3 substituents selected from the group consisting of F, Cl, CF$_3$, methyl, methoxy and NR(7)R(8);
  R(7) and R(8)
    independently of one another are hydrogen or alkyl having 1, 2, 3 or 4 carbon atoms;
where one of the substituents R(2) and R(3)
  is always defined as R(1);
R(4) and R(5)
  independently of one another are hydrogen, alkyl having 1, 2, 3 or 4 carbon atoms, alkoxy having 1, 2, 3 or 4 carbon atoms, F, Cl, Br, I, CN or —(CH$_2$)$_n$—(CF$_2$)$_o$—CF$_3$,
  n is zero or 1;
  o is zero or 1;
or its pharmaceutically tolerable salts.

2. A compound according to claim 1, wherein:
R(1) is H, F, Cl, Br, I, CN, NO$_2$, alkyl having 1, 2, 3, 4, 5, 6, 7, or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or X$_a$—(CF$_2$)$_c$—CF$_3$;
X is oxygen or sulfur;

a is zero or 1;
c is zero, 1, 2 or 3;
or
R(1) is —SR(10) or —OR(10);
R(10) is —$C_fH_{2f}$-cycloalkyl having 3, 4, 5, 6, 7 or 8 carbon atoms in the cycloalkyl ring, heteroaryl having 1, 2, 3, 4, 5, 6, 7, 8 or 9 carbon atoms or phenyl, where heteroaryl and phenyl are unsubstituted or are substituted by 1–3 substituents selected from the group consisting of F, Cl, $CF_3$, $CH_3$, methoxy, hydroxyl, amino, methylamino and dimethylamino;
f is zero or 1;
or
R(1) is phenyl, naphthyl, biphenylyl or heteroaryl having 1, 2, 3, 4, 5, 6, 7, 8 or 9 carbon atoms, the latter linked via a carbon or nitrogen atom of the ring,
each of which is unsubstituted or is substituted by 1–3 substituents selected from the group consisting of F, Cl, $CF_3$, $CH_3$, methoxy, hydroxyl, amino, methylamino and dimethylamino;
or
(R1) is —SR(13), —OR(13), —NHR(13), —NR(13)R(14), —C≡CR(18) or —C[R(19)]=CHR(18);
R(13) and R(14),
identically or differently, are —$(CH_2)_g$—$(CHOH)_h$—$(CH_2)_i$—$(CHOH)_{kk}$—R(17) or —$(CH_2)_g$—O—$(CH_2$—$CH_2O)_h$—R(24);
R(17) is hydrogen or methyl;
g, h and i,
identically or differently, are zero, 1 or 2;
kk is 1 or 2;
R(18) is phenyl,
which is unsubstituted or is substituted by 1–3 substituents selected from the group consisting of F, Cl, $CF_3$, methyl, methoxy and NR(25)R(26);
R(25) and R(26)
are H or alkyl having 1, 2, 3 or 4 carbon atoms;
or
R(18) is heteroaryl having 1, 2, 3, 4, 5, 6, 7, 8 or 9 carbon atoms, which is unsubstituted or is substituted as phenyl;
or
R(18) is cycloalkyl having 3, 4, 5, 6, 7 or 8 carbon atoms;
R(19) is hydrogen or methyl;
one of the substituents R(2) and R(3)
is —O—CO—R(27);
R(27) is alkyl having 1, 2, 3 or 4 carbon atoms, cycloalkyl having 3, 4, 5 or 6 carbon atoms, phenyl, biphenylyl, naphthyl, pyridyl or quinolinyl,
where phenyl, biphenylyl, naphthyl, pyridyl or quinolinyl are unsubstituted or substituted by 1–3 substituents selected from the group consisting of F, Cl, $CF_3$, methyl and methoxy;
and
the other of the substituents R(2) and R(3)
in each case is defined as R(1);
R(4) and R(5)
are hydrogen, alkyl having 1 or 2 carbon atoms, alkoxy having 1 or 2 carbon atoms, F, Cl, CN or —$(CF_2)_o$—$CF_3$;
o is zero or 1;
where R(4) and R(5) are not simultaneously hydrogen.

3. A compound according to claim 2, wherein:
R(1) is H, F, Cl, alkyl having 1, 2, 3 or 4 carbon atoms, alkoxy having 1, 2, 3 or 4 carbon atoms, cycloalkyl having 5 or 6 carbon atoms or $X_a$—$CF_3$;
X is oxygen;
a is zero or 1;
or
R(1) is —SR(10) or —OR(10);
R(10) is cycloalkyl having 4, 5 or 6 carbon atoms, quinolyl, isoquinolyl, pyridyl or phenyl,
quinolyl, isoquinolyl and pyridyl being bonded via a carbon or nitrogen atom of their ring,
and phenyl being unsubstituted or substituted by 1–3 substituents selected from the group consisting of F, Cl, $CF_3$, $CH_3$, methoxy, hydroxyl, amino, methylamino and dimethylamino;
or
R(1) is quinolyl, isoquinolyl or pyridyl,
each of which is linked via a carbon or nitrogen atom of their ring,
or
(R1) is —C≡CR(18);
R(18) is phenyl or cycloalkyl having five or 6 carbon atoms,
R(2) and R(3)
are —O—CO—R(27);
R(27) is alkyl having 1, 2, 3 or 4 carbon atoms, cycloalkyl having 3, 4, 5 or 6 carbon atoms, phenyl, biphenylyl, naphthyl, pyridyl or quinolinyl,
where phenyl, biphenylyl, naphthyl, pyridyl or quinolinyl are unsubstituted or substituted by 1–3 substituents selected from the group consisting of F, Cl, $CF_3$, methyl and methoxy;
where one of the substituents R(2) and R(3)
is always defined as R(1);
R(4) and R(5)
independently of one another are methyl, methoxy, F, Cl, CN or $CF_3$.

4. A compound according to claim 1, wherein:
R(1) is H, F, Cl, alkyl having 1, 2, 3 or 4 carbon atoms, alkoxy having 1, 2, 3 or 4 carbon atoms, cycloalkyl having 5 or 6 carbon atoms, cycloalkoxy having 5 or 6 carbon atoms or $CF_3$;
one of the substituents R(2) and R(3)

is —O—CO—$CH_3$;

and
the other of the substituents R(2) and R(3)
in each case is defined as R(1);
R(4) and R(5)
are methyl, methoxy, F, Cl, CN or $CF_3$;
where R(4) and R(5)
are not simultaneously hydrogen.

5. A method of treating Ilnesses caused by ischemic conditions, which comprises, administering to a patient in need thereof an effective amount of a compound of claim 1.

6. A method of treating illnesses caused by ischemic conditions, which comprises mixing an effective quantity of a compound I as claimed in claim 1 with the customary additives, and administering the mixture in a suitable form for administration.

7. A method of treating cardiac infarct and arrhythmias comprising administering to a patient in need thereof an effective amount of a compound of claim 1.

8. A method of treating angina pectoris comprising administering to a patient an effective amount of a compound of claim 1.

9. A method of treating ischemic conditions of the heart comprising administering to a patient an effective amount of a compound of claim 1.

10. A method of treating ischemic conditions of the peripheral and central nervous system and of stroke comprising administering to a patient an effective amount of a compound of claim 1.

11. A method of treating ischemic conditions of peripheral organs and limbs comprising administering to a patient an effective amount of a compound of claim 1.

12. A method of treating states of shock comprising administering to a patient an effective amount of a compound of claim 1.

13. A method of conducting surgical operations and organ transplatations comprising using a compound according to claim 1.

14. A method of preserving and storing transplants for surgical measures comprising using a compound according to claim 1.

15. A method of treating diseases in which cell proliferation is a primary or secondary cause, comprising administering to a patient an effective amount of a compound according to claim 1.

16. The method of claim 15 wherein the disease is atherosclerosis, diabetic late complications, carcinomatous disorders, fibrotic disorders and prostate hyperplasia.

17. The method of claim 16 wherein the fibrotic disorder is pulmonary fibrosis, hepatic fibrosis or renal fibrosis.

18. A method of treating disorders of lipid metabolism comprising administering to a patient an effective amount of a compound according to claim 1.

19. A medicine, comprising an effective amount of a compound according to claim 1.

* * * * *

UNITED STATES PATENT AND TRADEMARK OFFICE
CERTIFICATE OF CORRECTION

PATENT NO.  : 6,011,063
DATED       : January 4, 2000
INVENTOR(S) : Andreas Weichert et al.

It is certified that error appears in the above-identified patent and that said Letters Patent is hereby corrected as shown below:

Column 11,
In the structure for fomual I,

" 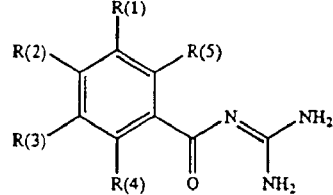 „ should read -- 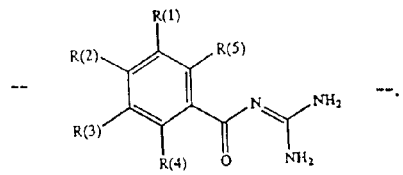 --.

Column 14,
Line 51, "llnesses" should read -- illnesses --.

Column 15,
Line 12, "transplatations" should read -- transplantations --.

Signed and Sealed this

Eighth Day of October, 2002

Attest:

*Attesting Officer*

JAMES E. ROGAN
*Director of the United States Patent and Trademark Office*